United States Patent
DeLuca et al.

(10) Patent No.: US 10,519,246 B2
(45) Date of Patent: Dec. 31, 2019

(54) ANTI-FIBROBLAST ACTIVATION PROTEIN (FAP) ANTIBODIES FOR TREATMENT AND DIAGNOSIS

(71) Applicant: Philogen S.P.A., Siena (IT)

(72) Inventors: Roberto DeLuca, Rivera (CH); Catherine Pemberton Ross, Brugg (CH)

(73) Assignee: Philogen SPA, Siena (IT)

( * ) Notice: Subject to any disclaimer, the term of this patent is extended or adjusted under 35 U.S.C. 154(b) by 244 days.

(21) Appl. No.: 15/544,367

(22) PCT Filed: Jan. 18, 2016

(86) PCT No.: PCT/EP2016/050890
§ 371 (c)(1),
(2) Date: Jul. 18, 2017

(87) PCT Pub. No.: WO2016/116399
PCT Pub. Date: Jul. 28, 2016

(65) Prior Publication Data
US 2018/0186891 A1    Jul. 5, 2018

(30) Foreign Application Priority Data
Jan. 19, 2015 (GB) .................................. 1500875.8

(51) Int. Cl.
| | |
|---|---|
| *C07K 16/30* | (2006.01) |
| *C07K 16/40* | (2006.01) |
| *A61P 37/06* | (2006.01) |
| *A61P 35/00* | (2006.01) |
| *A61K 39/395* | (2006.01) |
| *A61K 39/00* | (2006.01) |

(52) U.S. Cl.
CPC ........ *C07K 16/30* (2013.01); *A61K 39/39558* (2013.01); *A61P 35/00* (2018.01); *A61P 37/06* (2018.01); *C07K 16/40* (2013.01); *A61K 2039/505* (2013.01); *A61K 2039/572* (2013.01)

(58) Field of Classification Search
None
See application file for complete search history.

(56) References Cited

U.S. PATENT DOCUMENTS

2012/0258119 A1    10/2012    Renner et al.

FOREIGN PATENT DOCUMENTS

| EP | 1806365 A1 | 7/2007 |
| WO | 2011/020783 A2 | 2/2011 |
| WO | 2011/040972 A1 | 4/2011 |
| WO | 2012/020006 A2 | 2/2012 |

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Goldstein, L.A., et al., "Molecular cloning of seprase: a serine integral membrane protease from human melanoma" Biochimica et Biophysica Acta (1997) 1361:11-19.
Morimoto, C., et al., "The structure and function of CD26 in the T-cell immune response" Immunological Reviews (1998) 161:55-70.
Niedermeyer, J., et al. "Mouse fibroblast-activation protein: Conserved Fap gene organization and biochemical function as a serine protease" Eur. J. Biochem. (1998) 254:650-654.
Zhang, J., et al., "Identification of inhibitory scFv antibodies targeting fibroblast activation protein utilizing phage display functional screens" FASEB J. (2013) 27:581-589.
Brocks, B., "Species-Crossreactive scFv Against the Tumor Stroma Marker "Fibroblast Activation Protein" Selected by Phage Display From an Immunized FAP-I-Knock-Out Mouse" Molecular Medicine (2001) 7(7):461-469.
Schmidt, A., et al., "Generation of human high-affinity antibodies specific for the fibroblast activation protein by guided selection" Eur. J. Biochem. (2001) 268:1730-1738.
Welt, S., et al., "Antibody Targeting in Metastatic Colon Cancer: A Phase I Study of Monoclonal Antibody F19 Against a Cell-Surface Protein of Reactive Tumor Stromal Fibroblasts" J. Clin. Oncol. (1994) 12:1193-1203.
Mersmann, M., et al., "Human Antibody Derivatives Against the Fibroblast Activation Protein for Tumor Stroma Targeting of Carcinomas" Int. J. Cancer (2001) 92:240-248.
Ostermann, E., et al., "Effective Immunoconjugate Therapy in Cancer Models Targeting a Serine Protease of Tumor Fibroblasts" Clin. Cancer Res. (2008) 14(14):4584-4592.
Wuest, T., et al., "Construction of a bispecific single chain antibody for recruitment of cytotoxic T cells to the tumor stroma associated antigen fibroblast activation protein" J. Biotech. (2001) 92:159-168.
Fischer, E., et al., "Radioimmunotherapy of Fibroblast Activation Protein Positive Tumors by Rapidly Internalizing Antibodies" Clin. Cancer Res. (2012) 18(22):6208-6218.
Occhino, M., et al., "Generation and characterization of dimeric small immunoproteins specific for neuroblastoma associated antigen GD2" Intl. J. Mol. Med. (2004) 14:383-388.

* cited by examiner

*Primary Examiner* — Meera Natarajan
(74) *Attorney, Agent, or Firm* — Kathleen D. Rigaut; Howson & Howson LLP (57) ABSTRACT

The present invention relates to the diagnosis and treatment of diseases, such as cancer and inflammatory disorders. The invention provides, and involves the use of, antibodies that bind fibroblast activation protein (FAP).

13 Claims, 3 Drawing Sheets
Specification includes a Sequence Listing.

SEQUENCE LISTING

<160> NUMBER OF SEQ ID NOS: 9

<210> SEQ ID NO 1
<211> LENGTH: 116
<212> TYPE: PRT
<213> ORGANISM: Artificial sequence
<220> FEATURE:
<223> OTHER INFORMATION: VH of antibody F5 specific for fibroblast
      activation protein (FAP)

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Ala
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Arg Ala Phe Asp Tyr Trp Gly Gln Gly Thr Leu Val
            100                 105                 110

Thr Val Ser Ser
        115

<210> SEQ ID NO 2
<211> LENGTH: 108
<212> TYPE: PRT
<213> ORGANISM: Artificial sequence
<220> FEATURE:
<223> OTHER INFORMATION: VL of antibody F5 specific for fibroblast
      activation protein (FAP)

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Leu Gly Tyr Pro
                85                  90                  95

Pro Thr Phe Gly Gln Gly Thr Lys Val Glu Ile Lys
            100                 105

<210> SEQ ID NO 3
<211> LENGTH: 10
<212> TYPE: PRT
<213> ORGANISM: Artificial sequence
<220> FEATURE:
<223> OTHER INFORMATION: VH CDR1 of antibody F5 specific for fibroblast
      activation protein (FAP)

<400> SEQUENCE: 3

Gly Phe Thr Phe Ser Pro Ala Tyr Met Ser
1               5                   10

<210> SEQ ID NO 4
<211> LENGTH: 17
<212> TYPE: PRT
<213> ORGANISM: Artificial sequence
<220> FEATURE:
<223> OTHER INFORMATION: VH CDR2 of antibody F5 specific for fibroblast
      activation protein (FAP)

<400> SEQUENCE: 4

Ala Ile Ser Gly Ser Gly Gly Ser Thr Tyr Tyr Ala Asp Ser Val Lys
1               5                   10                  15

Gly

<210> SEQ ID NO 5
<211> LENGTH: 7
<212> TYPE: PRT
<213> ORGANISM: Artificial sequence
<220> FEATURE:
<223> OTHER INFORMATION: VH CDR3 of antibody F5 specific for fibroblast
      activation protein (FAP)

<400> SEQUENCE: 5

Gly Trp Arg Ala Phe Asp Tyr
1               5

<210> SEQ ID NO 6
<211> LENGTH: 12
<212> TYPE: PRT
<213> ORGANISM: Artificial sequence
<220> FEATURE:
<223> OTHER INFORMATION: VL CDR1 of antibody F5 specific for fibroblast
      activation protein (FAP)

<400> SEQUENCE: 6

Arg Ala Ser Gln Ser Val Ser Arg Asn Tyr Leu Ala
1               5                   10

<210> SEQ ID NO 7
<211> LENGTH: 7
<212> TYPE: PRT
<213> ORGANISM: Artificial sequence
<220> FEATURE:
<223> OTHER INFORMATION: VL CDR2 of antibody F5 specific for fibroblast
      activation protein (FAP)

<400> SEQUENCE: 7
```

-continued

Gly Ala Ser Ser Arg Ala Thr
1               5

<210> SEQ ID NO 8
<211> LENGTH: 9
<212> TYPE: PRT
<213> ORGANISM: Artificial sequence
<220> FEATURE:
<223> OTHER INFORMATION: VL CDR3 of antibody F5 specific for fibroblast
      activation protein (FAP)

<400> SEQUENCE: 8

Gln Gln Ser Leu Gly Tyr Pro Pro Thr
1               5

<210> SEQ ID NO 9
<211> LENGTH: 741
<212> TYPE: PRT
<213> ORGANISM: Artificial sequence
<220> FEATURE:
<223> OTHER INFORMATION: Amino acid sequence of the histidine-tagged
      recombinant protein corresponding to the FAP extracellular domain
      (residues 26-760) used to isolate the F5 antibody

<400> SEQUENCE: 9

Leu Arg Pro Ser Arg Val His Asn Ser Glu Glu Asn Thr Met Arg Ala
1               5                   10                  15

Leu Thr Leu Lys Asp Ile Leu Asn Gly Thr Phe Ser Tyr Lys Thr Phe
                20                  25                  30

Phe Pro Asn Trp Ile Ser Gly Gln Glu Tyr Leu His Gln Ser Ala Asp
            35                  40                  45

Asn Asn Ile Val Leu Tyr Asn Ile Glu Thr Gly Gln Ser Tyr Thr Ile
    50                  55                  60

Leu Ser Asn Arg Thr Met Lys Ser Val Asn Ala Ser Asn Tyr Gly Leu
65                  70                  75                  80

Ser Pro Asp Arg Gln Phe Val Tyr Leu Glu Ser Asp Tyr Ser Lys Leu
                85                  90                  95

Trp Arg Tyr Ser Tyr Thr Ala Thr Tyr Tyr Ile Tyr Asp Leu Ser Asn
            100                 105                 110

Gly Glu Phe Val Arg Gly Asn Glu Leu Pro Arg Pro Ile Gln Tyr Leu
        115                 120                 125

Cys Trp Ser Pro Val Gly Ser Lys Leu Ala Tyr Val Tyr Gln Asn Asn
    130                 135                 140

Ile Tyr Leu Lys Gln Arg Pro Gly Asp Pro Pro Phe Gln Ile Thr Phe
145                 150                 155                 160

Asn Gly Arg Glu Asn Lys Ile Phe Asn Gly Ile Pro Asp Trp Val Tyr
                165                 170                 175

Glu Glu Glu Met Leu Ala Thr Lys Tyr Ala Leu Trp Trp Ser Pro Asn
            180                 185                 190

Gly Lys Phe Leu Ala Tyr Ala Glu Phe Asn Asp Thr Asp Ile Pro Val
        195                 200                 205

Ile Ala Tyr Ser Tyr Tyr Gly Asp Glu Gln Tyr Pro Arg Thr Ile Asn
    210                 215                 220

Ile Pro Tyr Pro Lys Ala Gly Ala Lys Asn Pro Val Val Arg Ile Phe
225                 230                 235                 240

Ile Ile Asp Thr Thr Tyr Pro Ala Tyr Val Gly Pro Gln Glu Val Pro
                245                 250                 255

Val Pro Ala Met Ile Ala Ser Ser Asp Tyr Tyr Phe Ser Trp Leu Thr
            260                 265                 270

-continued

```
Trp Val Thr Asp Glu Arg Val Cys Leu Gln Trp Leu Lys Arg Val Gln
        275                 280                 285

Asn Val Ser Val Leu Ser Ile Cys Asp Phe Arg Glu Asp Trp Gln Thr
290                 295                 300

Trp Asp Cys Pro Lys Thr Gln Glu His Ile Glu Glu Ser Arg Thr Gly
305                 310                 315                 320

Trp Ala Gly Gly Phe Phe Val Ser Thr Pro Val Phe Ser Tyr Asp Ala
                325                 330                 335

Ile Ser Tyr Tyr Lys Ile Phe Ser Asp Lys Asp Gly Tyr Lys His Ile
                340                 345                 350

His Tyr Ile Lys Asp Thr Val Glu Asn Ala Ile Gln Ile Thr Ser Gly
                355                 360                 365

Lys Trp Glu Ala Ile Asn Ile Phe Arg Val Thr Gln Asp Ser Leu Phe
        370                 375                 380

Tyr Ser Ser Asn Glu Phe Glu Glu Tyr Pro Gly Arg Arg Asn Ile Tyr
385                 390                 395                 400

Arg Ile Ser Ile Gly Ser Tyr Pro Pro Ser Lys Lys Cys Val Thr Cys
                405                 410                 415

His Leu Arg Lys Glu Arg Cys Gln Tyr Tyr Thr Ala Ser Phe Ser Asp
                420                 425                 430

Tyr Ala Lys Tyr Tyr Ala Leu Val Cys Tyr Gly Pro Gly Ile Pro Ile
                435                 440                 445

Ser Thr Leu His Asp Gly Arg Thr Asp Gln Glu Ile Lys Ile Leu Glu
        450                 455                 460

Glu Asn Lys Glu Leu Glu Asn Ala Leu Lys Asn Ile Gln Leu Pro Lys
465                 470                 475                 480

Glu Glu Ile Lys Lys Leu Glu Val Asp Glu Ile Thr Leu Trp Tyr Lys
                485                 490                 495

Met Ile Leu Pro Pro Gln Phe Asp Arg Ser Lys Lys Tyr Pro Leu Leu
                500                 505                 510

Ile Gln Val Tyr Gly Gly Pro Cys Ser Gln Ser Val Arg Ser Val Phe
        515                 520                 525

Ala Val Asn Trp Ile Ser Tyr Leu Ala Ser Lys Glu Gly Met Val Ile
530                 535                 540

Ala Leu Val Asp Gly Arg Gly Thr Ala Phe Gln Gly Asp Lys Leu Leu
545                 550                 555                 560

Tyr Ala Val Tyr Arg Lys Leu Gly Val Tyr Glu Val Glu Asp Gln Ile
                565                 570                 575

Thr Ala Val Arg Lys Phe Ile Glu Met Gly Phe Ile Asp Glu Lys Arg
                580                 585                 590

Ile Ala Ile Trp Gly Trp Ser Tyr Gly Gly Tyr Val Ser Ser Leu Ala
        595                 600                 605

Leu Ala Ser Gly Thr Gly Leu Phe Lys Cys Gly Ile Ala Val Ala Pro
610                 615                 620

Val Ser Ser Trp Glu Tyr Tyr Ala Ser Val Tyr Thr Glu Arg Phe Met
625                 630                 635                 640

Gly Leu Pro Thr Lys Asp Asp Asn Leu Glu His Tyr Lys Asn Ser Thr
                645                 650                 655

Val Met Ala Arg Ala Glu Tyr Phe Arg Asn Val Asp Tyr Leu Leu Ile
                660                 665                 670

His Gly Thr Ala Asp Asp Asn Val His Phe Gln Asn Ser Ala Gln Ile
                675                 680                 685
```

-continued

```
Ala Lys Ala Leu Val Asn Ala Gln Val Asp Phe Gln Ala Met Trp Tyr
    690             695             700
Ser Asp Gln Asn His Gly Leu Ser Gly Leu Ser Thr Asn His Leu Tyr
705             710             715             720
Thr His Met Thr His Phe Leu Lys Gln Cys Phe Ser Leu Ser Asp His
            725             730             735
His His His His His
            740
```

ANTI-FIBROBLAST ACTIVATION PROTEIN (FAP) ANTIBODIES FOR TREATMENT AND DIAGNOSIS

CROSS-REFERENCE TO RELATED APPLICATIONS

This application is a 371 of International Application No. PCT/EP2016/050890, filed Jan. 18, 2016, which claims priority from Great Britain Application No, 1500875.8, filed Jan. 19, 2015. The entire disclosure of each of the aforesaid applications is incorporated by reference in the present application.

FIELD OF THE INVENTION

The present invention relates to the diagnosis and treatment of diseases, including cancer and inflammatory disorders. The invention provides, and involves the use of, antibodies that bind fibroblast activation protein (FAP).

BACKGROUND TO THE INVENTION

Most conventional pharmaceuticals currently in use for the treatment of serious disorders such as cancer and inflammatory diseases do not selectively accumulate at the site of disease [Bosslet et al., 58, 1195-1201 Cancer Res. (1998)]. For example, intravenously administered drugs distribute evenly within the different organs and tissues of the body, rather than selectively accumulating at the site of disease.

One approach to circumvent the disadvantages of conventional pharmacological therapies involves the preferential delivery of a bioactive agent to the site of disease by means of a binding molecule specific for a pathology-associated marker [Neri & Bicknell (2005), 5, 436-446 Nature Rev. Cancer]. The selective targeting of the drug to the diseased tissue will ultimately result in an increased local concentration at its site of action, sparing normal organs from the unwanted effects of the bioactive agent used to confer a pharmacological benefit (e.g., a growth factor, an enzyme, a hormone, an anti-inflammatory drug, a cytotoxic drug, a cytokine, a radionuclide, a photosensitizer). In most cases, this will lead to an improved therapeutic index of the delivered pharmaceutical, i.e. a higher efficacy with minimized side effects. Indeed, the favourable toxicity profile of site-specific therapeutics may open new avenues in the therapy of angiogenesis-related diseases, allowing the systemic administration of highly potent and promising agents, which are currently either given at suboptimal doses or whose clinical application has to date been impeded by unacceptable side-effects when applied in an unmodified form.

Ligand-based pharmacodelivery strategies fundamentally rely on the identification of good-quality markers of pathology, allowing a clear-cut discrimination between diseased tissues and healthy organs. Monoclonal antibodies and their fragments represent the preferred agents for pharmacodelivery applications [Rybak et al. 2, 22-40 Chem. Med. Chem (2007); Shrama et al., 5, 147-159 Nat. Rev. Drug Discovery (2006)], but globular protein mutants [Binz and Plückthun, 23, 1257-1268 Nature Biotechnology (2005)], peptides [Sergeeva et al., 58, 1622-1654, Adv. Drug. Deliv. Rev. (2006)] and even small organic ligands [Low et al., 41, 120-129, Acc. Chem. Res. (2008)] are also increasingly being used.

Antibody-based targeted delivery of bioactive agents to sites of angiogenesis as a therapeutic strategy for cancer treatment has been described. In the case of inflammatory disorders, antibody-based targeted delivery is much less well studied. The applicant has previously demonstrated that the ED-A domain of fibronectin, and the ED-B domain of fibronectin, two marker of angiogenesis, are expressed in the arthritic paws in the collagen-induced mouse model of rheumatoid arthritis. Using both radioactive and fluorescent techniques, the human monoclonal antibody F8, specific to ED-A, and the human monoclonal antibody L19, specific to ED-B, were found to selectively localize at sites of inflammation in vivo, following intravenous administration. When such antibodies were fused to the anti-inflammatory cytokine interleukin-10 the conjugate strong therapeutic activity was also shown (PCT/EP2007/004044, PCT/EP2008/009070). Nevertheless there remains a need in the art for further antibodies which can be employed in ligand-based pharmacodelivery applications for the treatment and diagnosis of diseases, such as cancer and inflammatory disorders.

Fibroblast Activation Protein (FAP)

Fibroblast activation protein (FAP) is a 95-kDa, cell surface-bound, type II transmembrane glycoprotein and belongs to the family of serine prolyl oligopeptidases. FAP is essentially identical to seprase [Goldstein et al., Biochim. Biophys. Acta. 1361(1), 11-19 (1997)], and closely related to dipeptidylpeptidase IV (DPP IV), also known as CD26, another type II integral membrane protein [Morimoto et al., Immunol Rev., 161, 55-70, (1998)]. It is selectively expressed in reactive stromal fibroblasts of epithelial cancers, granulation tissue of healing wounds, and malignant cells of bone and soft tissue sarcomas. This protein is thought to be involved in the control of fibroblast growth or epithelial-mesenchymal interactions during development, tissue repair, and epithelial carcinogenesis.

There is 89% homology between murine and human FAP [Niedermeyer et al., Eur. J. Biochem., 254(3), 650-654, (1998)].

SUMMARY OF THE INVENTION

The present invention relates to the provision of novel antibody molecules for use in therapeutic and/or diagnostic applications. In particular, the antibody molecules of the present invention find use in pharmacodelivery applications.

Specifically, the present inventors have isolated novel antibody molecules which bind fibroblast activation protein (FAP), and have shown that these antibody molecules are capable of targeting vascular structures, including the neovasculature of tumour tissues. The antibodies of the invention are also expected to be capable of targeting neovasculature associated with inflammatory disorders and autoimmune diseases, such as rheumatoid arthritis (RA), and Inflammatory bowel disease. These antibody molecules can thus be used for the targeted delivery of therapeutic and/or diagnostic agents to the neovasculature for which there is a continued need.

In a first aspect, the present invention relates to an antibody molecule that binds fibroblast activation protein (FAP). The fibroblast activation protein (FAP), is preferably human fibroblast activation protein (FAP). The antibody molecule preferably comprises the HCDR3 of the F5 antibody molecule set forth in SEQ ID NO: 5, or an HCDR3 with the amino acid sequence set forth in SEQ ID NO: 5 with three or fewer amino acid substitutions, deletions, or insertions. In addition, the antibody molecule may comprise the HCDR1, HCDR2, LCDR1, LCDR2, and/or LCDR3 sequences of the F5 antibody molecule set forth in SEQ ID NOs 3-5 and 6-8. For example, the antibody molecule may comprise the VH domain and/or VL domain of the F5 antibody molecule set forth in SEQ ID NOs 1 and 2, respectively.

As mentioned above, an antibody molecule of the invention may comprise a HCDR3 sequence as disclosed herein with three or fewer amino acid substitutions, deletions, or insertions. For example, an antibody molecule of the invention may comprise a HCDR3 sequence as disclosed herein with two or fewer, or one, amino acid substitution(s), deletion(s), or insertion(s). As with regard to the HCDR3 sequences, an antibody molecule of the invention may comprise a HCDR1, HCDR2, LCDR1, LCDR2, and/or LCDR3 sequence, as disclosed herein, with three or fewer, two or fewer, or one, amino acid substitution(s), deletion(s), or insertion(s). Similarly, and antibody molecule of the invention may comprise a VH and/or VL domain sequence as disclosed with ten or fewer, e.g. nine or fewer, eight or fewer, seven or fewer, six or fewer, five or fewer, four or fewer, three or fewer, two or fewer, or one, amino acid substitution(s), deletion(s), or insertion(s).

An antibody molecule, as referred to herein, may be in any suitable format. Many antibody molecule formats are known in the art and include both complete antibody molecule molecules, such as IgG, as well as antibody molecule fragments, such as a single chain Fv (scFv). The term "antibody molecule" as used herein encompasses both complete antibody molecule molecules and antibody molecule fragments, in particular antigen-binding fragments. Preferably, an antibody molecule comprises a VH domain and a VL domain. In a preferred embodiment, the antibody molecule is or comprises a scFv, is a small immunoprotein (SIP), is a diabody, or is a (complete) IgG molecule.

An antibody molecule of the present invention may be conjugated to a molecule to provide a conjugate. The choice of molecule conjugated to the antibody molecule will depend on the intended application of the conjugate. For example, where the conjugate is intended for the treatment of a disease or disorder, the conjugate may comprise an antibody molecule of the invention and a biocidal molecule, a cytotoxic molecule, a radioisotope, a photosensitizer, an enzyme, a hormone, an anti-inflammatory agent, an immunosuppressive agent, or a cytokine. Where the conjugate is intended for use in imaging, detecting, or diagnosing a disease or disorder, the conjugate may comprise an antibody molecule of the invention and a detectable label, such as a radioisotope, e.g. a non-therapeutic radioisotope. Depending on the molecule conjugated to the antibody molecule, the conjugate may be or may comprise a single chain protein. When the conjugate is a single chain protein, the entire protein can be expressed as a single polypeptide or fusion protein. In this case, the molecule may be conjugated to the antibody molecule by means of a peptide linker. Fusion proteins have the advantage of being easier to produce and purify since they consist of one single species. This facilitates production of clinical-grade material. Alternatively, the molecule may be conjugated to the antibody molecule by means of a cleavable linker.

The invention also provides isolated nucleic acids encoding the antibodies and conjugates of the invention. The skilled person would have no difficulty in preparing such nucleic acids using methods well-known in the art. An isolated nucleic acid may be used to express the antibody molecule or conjugate of the invention, for example by expression in a bacterial, yeast, insect or mammalian host cell. A preferred host cell is *E. coli*. The nucleic acid will generally be provided in the form of a recombinant vector for expression. Host cells in vitro comprising such vectors are part of the invention, as is their use for expressing the antibodies and conjugates of the invention, which may subsequently be purified from cell culture and optionally formulated into a pharmaceutical composition.

An antibody molecule or conjugate of the invention may be provided for example in a pharmaceutical composition, and may be employed for medical use as described herein, either alone or in combination with one or more further therapeutic agents. Alternatively, the antibody molecule or conjugate of the invention may be provided in a diagnostic composition and may be employed for diagnostic use as described herein.

In a second aspect, the invention relates to an antibody molecule or conjugate of the invention for use in a method for treatment of the human or animal body by therapy. For example, an antibody molecule or conjugate of the invention may for use in a method of treating an inflammatory disorder, inhibiting angiogenesis, treating cancer, and/or treating an autoimmune disease in a patient. The invention also relates to a method of treating an inflammatory disorder, inhibiting angiogenesis, treating cancer, and/or treating an autoimmune disease in a patient, the method comprising administering a therapeutically effective amount of an antibody molecule or conjugate of the invention to the patient. The use of an antibody molecule or conjugate of the invention for the manufacture of a medicament for the treatment of an inflammatory disorder, inhibiting angiogenesis, treating cancer, and/or treating an autoimmune disease, is also contemplated. An inflammatory disorder or autoimmune disease, as referred to herein, may be inflammatory bowel disease, such Crohn's disease or ulcerative colitis.

In an third aspect, the invention relates to an antibody molecule of the invention for use in a method of delivering a molecule to sites of an inflammatory disorder, sites of neovasculature which are the result of angiogenesis, sites of cancer and/or sites of autoimmune disease in a patient. The invention also relates to a method of delivering a molecule to sites of an inflammatory disorder, sites of neovasculature which are the result of angiogenesis, sites of cancer and/or sites of autoimmune disease in a patient comprising administering to the patient an antibody molecule of the invention, wherein the antibody molecule is conjugated to the molecule.

In an fourth aspect, the invention relates to an antibody molecule or conjugate of the invention for use in a method of imaging, detecting, or diagnosing an inflammatory disorder, angiogenesis, cancer, and/or an autoimmune disease in a patient. The invention further relates to a method of imaging, detecting, or diagnosing an inflammatory disorder, angiogenesis, cancer, and/or an autoimmune disease in a patient comprising administering an antibody molecule or conjugate of the invention to the patient. Also encompassed within the scope of the invention is the use of an antibody molecule or conjugate of the invention for the manufacture of a diagnostic product for imaging, detecting, or diagnosing an inflammatory disorder, angiogenesis, cancer, and/or an autoimmune disease. A patient, as referred to herein, is preferably a human patient.

DETAILED DESCRIPTION

The invention includes the combination of the aspects and preferred features described except where such a combination is clearly impermissible or expressly avoided.

The present invention relates to an antibody which binds fibroblast activation protein (FAP).

Antibody Molecule

The term "antibody molecule" describes an immunoglobulin whether natural or partly or wholly synthetically produced. The term also covers any polypeptide or protein having a binding domain which is, or is substantially homologous to, an antibody binding domain. Examples of antibodies are the immunoglobulin isotypes and their isotypic subclasses; fragments which comprise an antigen binding domain such single chain diabodies. The antibody molecule or fragment thereof may be human or humanised. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the CDRs of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody molecule" should be construed as covering antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

The term "specific" may be used to refer to the situation in which the antibody molecule will not show any significant binding to molecules other than its specific binding partner(s). The term is also applicable where e.g. an antigen-binding site of an antibody molecule is specific for a particular epitope that is carried by a number of antigens, in which case the antibody molecule carrying the antigen-binding site will be able to bind to the various antigens carrying the epitope.

The antibody molecule may be monovalent or bivalent i.e. may have two antigen binding sites. Where the antibody molecule is bivalent, the two antigen binding sites may be identical or different. An "antigen binding site" describes the part of an antibody which comprises the area which specifically binds to and is complementary to part or all of an antigen. Where an antigen is large, an antibody molecule may only bind to a particular part of the antigen, which part is termed an epitope. An antigen binding site may be provided by one or more antibody variable domains (e.g. a so-called Fd antibody fragment consisting of a VH domain).

Preferably, an antigen binding site comprises an antibody light chain variable region (VL) and an antibody heavy chain variable region (VH).

An antibody molecule of the invention preferably comprises the HCDR3 of antibody F5. The HCDR3 is known to play a role in determining the specificity of an antibody molecule (Segal et al., (1974), PNAS, 71:4298-4302; Amit et al., (1986), Science, 233:747-753; Chothia et al., (1987), J. Mol. Biol., 196:901-917; Chothia et al., (1989), Nature, 342:877-883; Caton et al., (1990), J. Immunol., 144:1965-1968; Sharon et al., (1990a), PNAS, 87:4814-4817; Sharon et al., (1990b), J. Immunol., 144:4863-4869; Kabat et al., (1991b), J. Immunol., 147:1709-1719).

The antibody molecule may further comprise the HCDR1, HCDR2, LCDR1, LCDR2 and/or LCDR3 of antibody F5.

The antibody may also comprise the VH and/or VL domain of antibody F5.

An antibody molecule of the invention may have a VH domain having at least 70%, more preferably one of at least 75%, 80%, 85%, 90%, 95%, 96%, 97%, 98%, 99% or 100%, sequence identity to the VH domain of antibody F5.

An antibody molecule of the invention may have a VL domain having at least 70%, more preferably one of at least 75%, 80%, 85%, 90%, 95%, 96%, 97%, 98%, 99% or 100%, sequence identity to the VL domain of antibody F5.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

Variants of these VH and VL domains and CDRs may also be employed in antibody molecules for use in as described herein. Suitable variants can be obtained by means of methods of sequence alteration, or mutation, and screening.

Particular variants for use as described herein may include one or more amino acid sequence alterations (addition, deletion, substitution and/or insertion of an amino acid residue), may be less than about 20 alterations, less than about 15 alterations, less than about 10 alterations or less than about 5 alterations, 4, 3, 2 or 1.

Alterations may be made in one or more framework regions and/or one or more CDRs. In particular, alterations may be made in HCDR1, HCDR2 and/or HCDR3.

The antibody molecule may be a whole antibody or a fragment thereof, in particular an antigen-binding fragment thereof.

Whole antibodies include IgA, IgD, IgE, IgG or IgM. Preferably, the whole antibody is IgG.

Antigen-binding fragments of whole antibodies include (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al. (1989) Nature 341, 544-546; McCafferty et al., (1990) Nature, 348, 552-554; Holt et al. (2003) Trends in Biotechnology 21, 484-490), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. (1988) Science, 242, 423-426; Huston et al. (1988) PNAS USA, 85, 5879-5883); (viii) bispecific single chain Fv dimers (PCT/US92/09965) and (ix) "diabodies", multivalent or multispecific fragments constructed by gene fusion (WO2013/014149; WO94/13804; Holliger et al. (1993a), Proc. Natl. Acad. Sci. USA 90 6444-6448). Fv, scFv or diabody molecules may be stabilized by the incorporation of disulphide bridges linking the VH and VL domains (Reiter et al. (1996), Nature Biotech, 14, 1239-1245). Minibodies comprising a scFv joined to a CH3 domain may also be made (Hu et al. (1996), Cancer Res., 56(13):3055-61). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

A single chain Fv (scFv) may be comprised within a mini-immunoglobulin or small immunoprotein (SIP), e.g. as described in (Li et al., (1997), Protein Engineering, 10: 731-736). An SIP may comprise an scFv molecule fused to the CH4 domain of the human IgE secretory isoform IgE-S2 ($\varepsilon_{S2}$-CH4; Batista et al., (1996), J. Exp. Med., 184: 2197-205) forming an homo-dimeric mini-immunoglobulin antibody molecule Preferably the antibody molecule comprises or consists of a single chain Fv, a small immunoprotein, a diabody, or a (whole) IgG molecule.

Conjugates

Conjugates of the invention comprise an antibody molecule of the invention and a therapeutic or diagnostic agent. The therapeutic agent may be a biocidal molecule, a cytotoxic molecule, a radioisotope, a photosensitizer, an enzyme, a hormone, an anti-inflammatory agent, or an immunosuppressive agent. Preferably, the therapeutic agent is a biocidal molecule, a cytotoxic molecule, a radioisotope, an anti-inflammatory agent. or an immunosuppressive agent. The biocidal molecule, cytotoxic molecule, anti-inflammatory agent, or an immunosuppressive agent may be a cytokine. An agent may have both immunosuppressive and anti-inflammatory activity.

The diagnostic agent may be radioisotope, e.g. a non-therapeutic radioisotope.

Radioisotopes which may be conjugated to a binding member of the invention include isotopes such as $^{94m}$Tc, $^{99m}$Tc, $^{186}$Re, $^{188}$Re, $^{203}$Pb, $^{67}$Ga, $^{68}$Ga, $^{47}$Sc, $^{111}$In, $^{97}$Ru, $^{62}$Cu, $^{64}$Cu, $^{86}$Y, $^{88}$Y, $^{90}$Y, $^{121}$Sn, $^{161}$Tb, $^{153}$Sm, $^{166}$Ho, $^{105}$Rh, $^{177}$Li, $^{123}$I, $^{124}$I, $^{125}$I, $^{131}$I, $^{18}$F, $^{211}$At and $^{225}$Ac. Preferably, positron emitters, such as $^{18}$F and $^{124}$I, or gamma emitters, such as $^{99m}$Tc, $^{111}$In and $^{123}$I, are used for diagnostic applications (e.g. for PET), while beta-emitters, such as $^{131}$I, $^{90}$Y and $^{177}$Lu, are preferably used for therapeutic applications. Alpha-emitters, such as $^{211}$At and $^{225}$AC may also be used for therapy. In one example, the specific binding member may be conjugated to $^{177}$Lu or $^{90}$Y.

The specific binding member may be conjugated with the therapeutic agent by means of a peptide bond or linker, i.e. within a fusion polypeptide comprising said molecule and the specific binding member or a polypeptide chain component thereof. Other means for conjugation include chemical conjugation, especially cross-linking using a bifunctional reagent (e.g. employing DOUBLE-REAGENTS™ Cross-linking Reagents Selection Guide, Pierce).

Linkers

The antibody molecule and the therapeutic or diagnostic agent may be connected to each other directly, for example through any suitable chemical bond or through a linker, for example a peptide linker.

The peptide linker may be a short (2-20, preferably 2-15, residue stretch of amino acids). Suitable examples of peptide linker sequences are known in the art. One or more different linkers may be used. The linker may be about 5 amino acids in length.

The chemical bond may be, for example, a covalent or ionic bond. Examples of covalent bonds include peptide bonds (amide bonds) and disulphide bonds. For example the antibody molecule and therapeutic or diagnostic agent may be covalently linked. For example by peptide bonds (amide bonds). Thus, the antibody molecule and therapeutic or diagnostic agent may be produced (secreted) as a single chain polypeptide. The individual components that form the antibody molecule or the therapeutic or diagnostic agent may also be connected directly, for example through any suitable chemical bond, or through a linker, for example a peptide linker. Examples of individual components which may be linked within the antibody molecule are CDRs or VH or VL sequences.

Methods of Treatment and Diagnosis

An antibody molecule or conjugate of the invention may be used in a method of treatment of the human or animal body, such as a method of treatment (which may include prophylactic treatment) of a disease or disorder in a patient (typically a human patient) comprising administering the antibody molecule or conjugate to the patient.

Accordingly, such aspects of the invention provide methods of treatment comprising administering an antibody molecule or conjugate of the invention, pharmaceutical compositions comprising such an antibody molecule or conjugate for the treatment of a condition or disease, and a method of making a medicament or pharmaceutical composition comprising formulating the antibody molecule or conjugate of the present invention with a physiologically acceptable carrier or excipient.

An antibody molecule or conjugate as herein described may be used in a method of treating an inflammatory disorder, inhibiting angiogenesis, treating cancer, and/or treating an autoimmune disease in a patient. An inflammatory disorder or autoimmune disease, as referred to herein, may be inflammatory bowel disease, such Crohn's disease or ulcerative colitis. The method may comprise targeting a therapeutic agent to the neovasculature in vivo. The agent may be any therapeutic agent discussed herein, which is suitable for treatment of the disease or disorder in question.

Also contemplated is a method of treating an inflammatory disorder, inhibiting angiogenesis, treating cancer, and/or treating an autoimmune disease in a patient by targeting a therapeutic agent to the neovasculature in a patient, the method comprising administering a therapeutically effective amount of an antibody molecule or conjugate as herein described to the patient.

An antibody molecule or conjugate as herein described may also be used in a method of imaging, detecting, or diagnosing a disease or disorder in a patient. A method of imaging, detecting, or diagnosing a disease or disorder comprising administering an antibody or conjugate as described herein to a patient is similarly contemplated. The disease or disorder may be an inflammatory disorder, angiogenesis, cancer, and/or an autoimmune disease. The method may comprise targeting a diagnostic agent, such as a detectable label, to the neovasculature in vivo.

Inflammatory disorders include any disease or disorder which is characterised by an inflammatory abnormality. Such disease include, for example, immune system disorders, such as autoimmune diseases, and cancer.

Angiogenesis is a feature of many known diseases and disorders and inhibition of angiogenesis using an antibody or conjugate of the invention may be used to treat such diseases and disorders. Similarly, diseases and disorders characterised by angiogenesis may be imaged, detected, or diagnosed using an antibody or conjugate described herein. Disease characterised by angiogenesis include, for example, rheumatoid arthritis, diabetic retinopathy, age-related muscular degeneration, angiomas, tumours and cancer.

As mentioned above, conditions which may be treated, imaged, detected, or diagnosed using an antibody or conjugate as described herein include cancer, as well as other tumours and neoplastic conditions.

Exemplary cancers include any type of solid or non-solid cancer or malignant lymphoma and especially liver cancer, lymphoma, leukaemia (e.g. acute myeloid leukaemia), sarcomas, skin cancer, bladder cancer, breast cancer, uterine cancer, ovarian cancer, prostate cancer, lung cancer, colorectal cancer, cervical cancer, head and neck cancer, oesophageal cancer, pancreatic cancer, renal cancer, stomach cancer and cerebral cancer. Cancers may be familial or sporadic. Cancers may be metastatic or non-metastatic. The cancer, tumour, or neoplastic condition may express fibroblast activation protein (FAP).

Autoimmune disease which may be treated, imaged, detected, or diagnosed using an antibody or conjugate as described herein include lupus erytematosus, rheumatoid arthritis, and psoriathic arthritis.

A further disease or disorder which may treated, imaged, detected, or diagnosed using an antibody or conjugate described herein is osteoarthritis.

Another disease or disorder which may treated, imaged, detected, or diagnosed using an antibody or conjugate described herein is IBD, such Crohn's disease or ulcerative colitis.

Pharmaceutical Compositions

A further aspect of the present invention relates to a pharmaceutical composition comprising at least one antibody molecule or conjugate of the invention and optionally a pharmaceutically acceptable excipient.

Pharmaceutical compositions of the present invention typically comprise a therapeutically effective amount of an antibody molecule or conjugate according to the invention and optionally auxiliary substances such as pharmaceutically acceptable excipient(s). Said pharmaceutical compositions are prepared in a manner well known in the pharmaceutical art. A carrier or excipient may be a liquid material which can serve as a vehicle or medium for the active ingredient. Suitable carriers or excipients are well known in the art and include, for example, stabilisers, antioxidants, pH-regulating substances, controlled-release excipients. The pharmaceutical composition of the invention may be adapted, for example, for parenteral use and may be administered to the patient in the form of solutions or the like.

Pharmaceutical compositions comprising the antibody molecule or conjugate of the present invention may be administered to a patient. Administration is preferably in a "therapeutically effective amount", this being sufficient to show benefit to the patient. Such benefit may be amelioration of at least one symptom. The actual amount administered, and rate and time-course of administration, will depend on the nature and severity of what is being treated. Prescription of treatment, e.g. decisions on dosage etc., is within the responsibility of general practitioners and other medical doctors. Treatments may be repeated at daily, twice-weekly, weekly, or monthly intervals at the discretion of the physician.

A pharmaceutical composition of the invention may be administered to a patient in need of treatment via any suitable route, usually by injection into the bloodstream and/or directly into the site to be treated. The precise dose and its frequency of administration will depend upon a number of factors, the route of treatment, the size and location of the area to be treated.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included For intravenous injection, or injection at the site of affliction, the pharmaceutical composition will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A pharmaceutical composition may be administered alone or in combination with other treatments, either simultaneously or sequentially dependent upon the condition to be treated.

Kits

Another aspect of the invention provides a therapeutic kit for use in the treatment of a disease or disorder comprising an antibody molecule or conjugate as described herein. The components of a kit are preferably sterile and in sealed vials or other containers.

A kit may further comprise instructions for use of the components in a method described herein. The components of the kit may be comprised or packaged in a container, for example a bag, box, jar, tin or blister pack.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1—Preparation and Characterization of a New Antibody Against Fibroblast Activation Protein (FAP)

The F5 antibody was isolated in scFv configuration from phage display libraries which include the libraries described in PCT/EP2009/006487, in Weber et al. (PLoS One, 2014, 9 (6) doi: 10/1361) and in Silacci et al. (Protein Engineering Design & Selection, 2006, 19, 471-478) according to the screening technique described by Silacci et al. (Protein Engineering Design & Selection, 2006, 19, 471-478).

The F5 antibody was isolated by screening the libraries against a recombinant fragment corresponding to the extracellular domain corresponding to residues 26-760 of FAP. The recombinant fragment also contained a C-terminal His6 tag. This recombinant fragment was produced in CHO.S cells and purified from the culture supernatant using nickel affinity chromatography. The sequence of this protein fragment is shown in SEQ ID NO: 9.

The cross-reactivity of the F5 antibody against human and mouse FAP was analysed by ELISA. The results shown in FIG. 1A, indicate that F5 recognize both mouse and human FAP. Binding of the F5 antibody was confirmed by Biacore probing the antigen at different concentrations (results shown in FIG. 1B).

Figure 1:
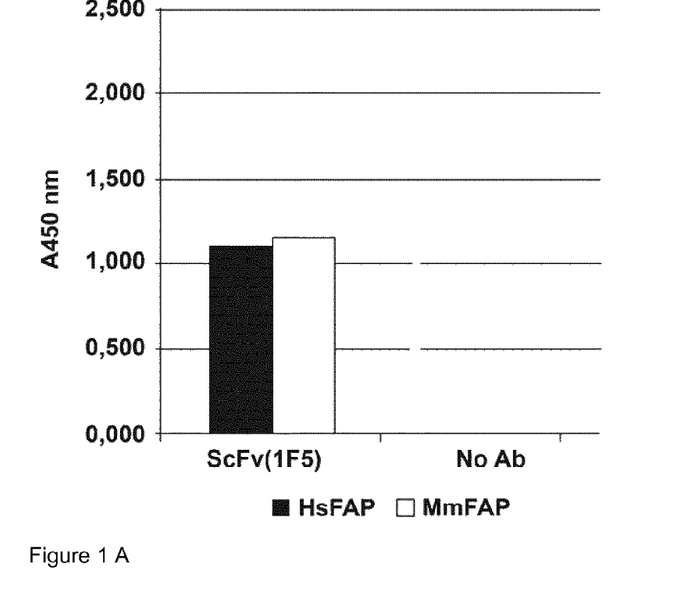
FIG. 1A shows the results of an ELISA demonstrating binding of antibody F5 (in scFv format) to both human and mouse FAP.
FIG. 1B shows Biacore data demonstrating binding of antibody F5 (in scFv format) at different concentrations to human FAP
FIG. 1C shows staining of tumor neovascolature for the F5 antibody (in SIP format) similar to the vascular targeting antibody F8 (in SIP format) as positive control. Negative control was performed using the irrelevant anti-lysozyme antibody KSF.

Finally, the F5 antibody displays good staining of neovascular structures as shown by immunofluorescence analyses. FIG. 1C shows staining human xenograft U87 (human primary glioblastoma) tumour sections taken from balb/c nu/nu mice, in which 10 μm thick tissue samples were stained with either (i) the anti-FAP antibody F5 in SIP format, (ii) the proven vascular targeting anti-ED-A antibody F8 as a positive control and (iii) anti-lysozyme antibody as a negative control antibody (red staining). All samples were also co-stained with an anti-CD31 antibody, an endothelial cell marker (green staining).

ELISA: Streptawell High Bind strips (Roche) were coated with biotinylated Human or Mouse FAP extracellular domain at 100 nM. Cross reactivity with human and murine antigen of the anti-FAP F5 antibody was assessed by detection with the anti-Myc antibody 9E10 and an HRP-conjugated anti-Murine $F_c$ antibody (Sigma). Calorimetric detection of antibody-antigen binding was performed using BM-Blue POD soluble substrate (Roche). Biacore analysis:

The F5 antibody was expressed as a scFv in CHO.S cells and purified from the culture supernatant by affinity chromatography using protein A resin (Sino Biological Inc.) The eluted fractions containing the F5 antibody were analysed for antigen binding by Biacore using a CM5 chip coated with the catalytic domain of human FAP extracellular domain. For $K_D$ determination, the purified antibodies were further analyzed by size-exclusion chromatography on a superdex 75 HR10/30 column (Amersham Biosciences), fractions across the peaks representing the ScFv monomer were collected and used at different nanomolar concentrations for affinity measurements by BIAcore on a low-density coated antigen chip.

Immunofluorescence on Tumor Sections:

Dual staining for FAP and the murine endothelial marker CD31 (BD Pharmingen) was performed on human xenograft U87 tumour sections taken from balb/c nu/nu mice. The 10 μm thickness frozen specimens were defrosted at room temperate and treated with ice-cold acetone, rehydrated in PBS and blocked with 3% BSA. The F5, F8 and KSF antibodies in SIP format were affinity purified from CHO.S cells (final concentration 5 mg/ml) and were incubated with the tissue sample. The binding of the antibody fragments to the tumour sections was assessed by detection with an anti-IgE antibody (Dako) (25 μg/ml). The vasculature was stained with the endothelial marker antibody (75pg/mL). The anti-IgE antibody was detected with goat anti-Rabbit Alexa 594 (Molecular Probes), and the anti-CD31 marker was detected using goat anti-rat IgG Alexa 488. DAPI was used for nuclei staining. The anti-hen egg Lysozyme antibody fragment SIP(KSF) was used as an isotype-negative control for the staining and the antibody fragment SIP(F8), specific to the extra domain A of fibronectin, was used as positive control.

Example 2—In Vivo Targeting Performance of FAP Antibodies

The ScFv-F5 and the ScFv-ESC11 (Fischer et al., 2012, Radioimmunotherapy of Fibroblast Activation Protein Positive Tumors by Rapidly Internalizing Antibodies, Clin. Cancer Res., 18, 6208-6218; Patent US20120258119 A1) were both cloned in Small Immuno-Protein (SIP) format. The proteins were expressed in CHO cells and purified over Protein A resin followed by a dialysis step in PBS.

In order to evaluate in vivo targeting performance, the SIP(F5) and the SIP(ESC11) antibodies were radio-iodinated with $^{125}I$ using Iodination tubes (Pierce), and purified on a PD-10 column. 10 μg of radio labelled antibody were injected intravenously into Balb/C nu/nu mice bearing subcutaneous U87 tumours (n=3). Mice were sacrificed 24 hours after injection. Organs were weighed and radioactivity was counted using a Cobra™ γ counter. The radioactivity content of representative organs is expressed as the mean±SE percent of the injected dose per gram of tissue.

Figure 2:
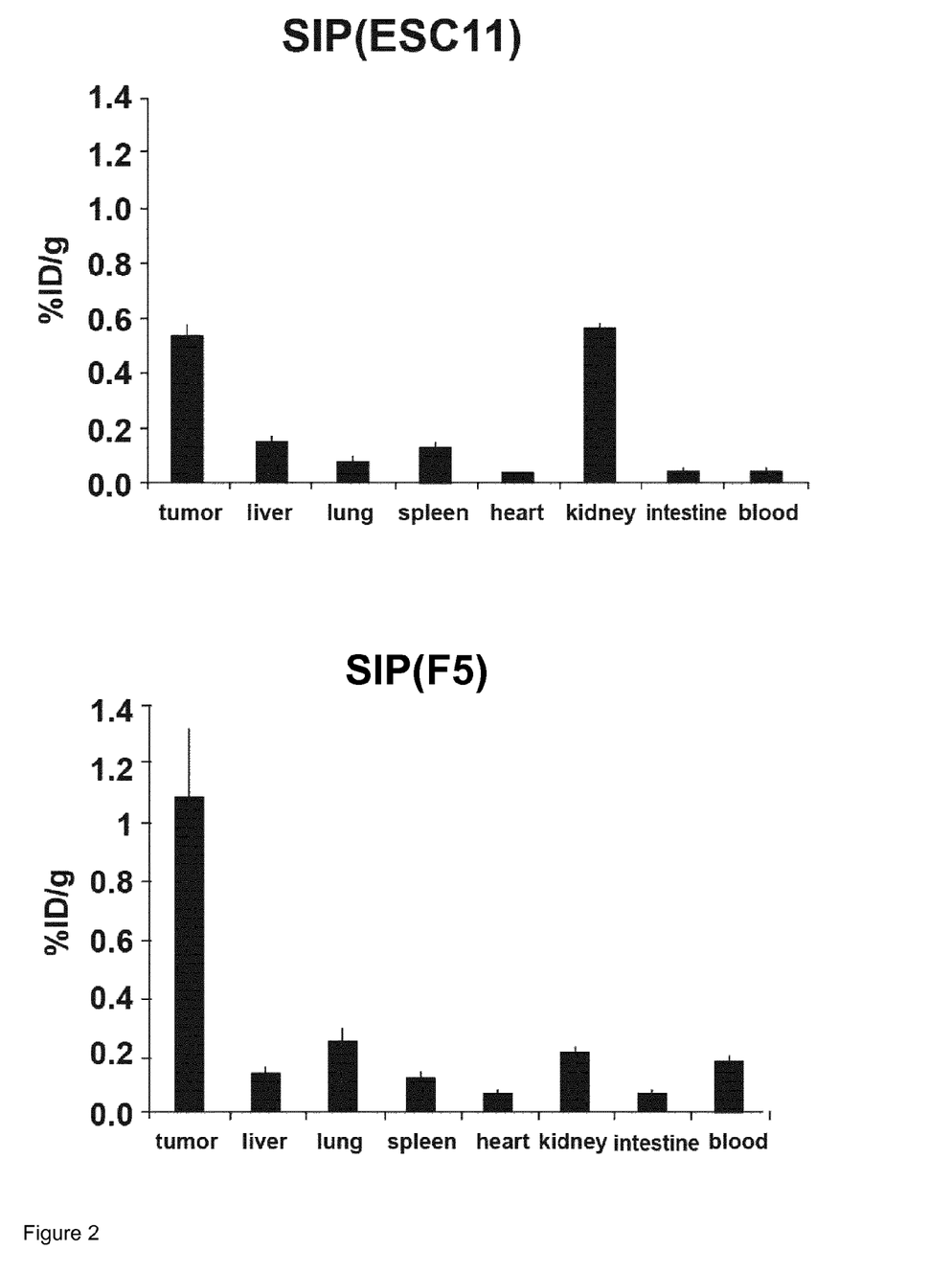
FIG. 2 shows the in vivo tumor targeting performance of the F5 antibody compared to a control anti-FAP antibody.

The results of this experiment are shown in FIG. 2. The SIP(F5) antibody showed preferential accumulation in the tumour; in the healthy organs the protein was not detected. The reference antibody SIP(ESC11) showed only little accumulation in the tumour; a comparable signal was also detected in the kidneys, suggesting a specific accumulation of the antibody in this healthy organ.

---

Sequence listing

Amino acid sequence of antibody F5 specific for
fibroblast activation protein (FAP)
SEQ ID NO: 1 (F5-VH)
EVQLLESGGGLVQPGGSLRLSCAASGFTFSPAYMSWVRQAPGKGLEWVSA
ISGSGGSTYYADSVKGRFTISRDNSKNTLYLQMNSLRAEDTAVYYCAKGW
RAFDYWGQGTLVTVSS SEQ ID NO: 2 (F5-VL)
EIVLIQSPGILSLSPGERATLSCRASQSVSRNYLAWYQQKPGQAPRLLIY
GASSRATGIPDRFSGSGSGTDFTLTISRLEPEDFAVYYCQQSLGYPPTFG
QGTKVEIK

SEQ ID NO: 3 (F5-VH CDR1)
GFTFSPAYMS

SEQ ID NO: 4 (F5-VH CDR2)
AISGSGGSTYYADSVKG

SEQ ID NO: 5 (F5-VH CDR3)
GWRAFDY

SEQ ID NO: 6 (F5-VL CDR1)
RASQSVSRNYLA

SEQ ID NO: 7 (F5-VL CDR2)
GASSRAT

Sequence listing

SEQ ID NO: 8 (F5-VL CDR3)
QQSLGYPPT

Amino acid sequence of the histidine-tagged
recombinant protein corresponding to the FAP
extracellular domain (residues 26-760) used to
isolate the F5 antibody
SEQ ID NO: 9
LRPSRVHNSEENTMRALTLKDILNGTFSYKTFFPNWISGQEYLHQSADNN
IVLYNIETGQSYTILSNRTMKSVNASNYGLSPDRQFVYLESDYSKLWRYS
YTATYYIYDLSNGEFVRGNELPRPIQYLCWSPVGSKLAYVYQNNIYLKQR
PGDPPFQITFNGRENKIFNGIPDWVYEEEMLATKYALWWSPNGKFLAYAE
FNDTDIPVIAYSYYGDEQYPRTINIPYPKAGAKNPVVRIFIIDTTYPAYV
GPQEVPVPAMIASSDYYFSWLTWVTDERVCLQWLKRVQNVSVLSICDFRE
DWQTWDCPKTQEHIEESRTGWAGGFFVSTPVFSYDAISYYKIFSDKDGYK
HIHYIKDTVENAIQITSGKWEAINIFRVTQDSLFYSSNEFEEYPGRRNIY
RISIGSYPPSKKCVTCHLRKERCQYYTASFSDYAKYYALVCYGPGIPIST
LHDGRTDQEIKILEENKELENALKNIQLPKEEIKKLEVDEITLWYKMILP
PQFDRSKKYPLLIQVYGGPCSQSVRSVFAVNWISYLASKEGMVIALVDGR
GTAFQGDKLLYAVYRKLGVYEVEDQITAVRKFIEMGFIDEKRIAIWGWSY
GGYVSSLALASGTGLFKCGIAVAPVSSWEYYASVYTERFMGLPTKDDNLE
HYKNSTVMARAEYFRNVDYLLIHGTADDNVHFQNSAQIAKALVNAQVDFQ
AMWYSDQNHGLSGLSTNHLYTHMTHFLKQCFSLSDHHHHHH

The invention claimed is:

1. An antibody molecule that binds fibroblast activation protein (FAP), wherein the antibody molecule comprises a VH domain comprising a framework and a set of complementarity determining regions HCDR1, HCDR2 and HCDR3, and a VL domain comprising a framework and a set of complementarity determining regions LCDR1, LCDR2 and LCDR3, wherein:

HCDR1 has the amino add sequence of SEQ ID NO: 3;
HCDR2 has the amino add sequence of SEQ ID NO: 4;
HCDR3 has the amino add sequence of SEQ ID NO: 5;
LCDR1 has the amino add sequence of SEQ ID NO: 6;
LCDR2 has the amino add sequence of SEQ ID NO: 7; and
LCDR3 has the amino add sequence of SEQ ID NO: 8.

2. The antibody molecule according to claim 1, wherein the VH domain has the amino acid sequence of SEQ ID NO: 1 or a sequence having 90% identity to SEQ ID NO: 1, and/or the VL domain has the amino acid sequence of SEQ ID NO: 2 or a sequence having 90% identity to SEQ ID NO: 2.

3. The antibody molecule according to claim 1, wherein the antibody molecule is or comprises a single chain Fv (scFv), is a small immunoprotein (SIP), is a diabody, or is an IgG molecule.

4. A conjugate comprising an antibody molecule according to claim 1 and an agent selected from a biocidal molecule, a cytotoxic molecule, a radioisotope and an inflammatory agent.

5. The conjugate according to claim 4, wherein the biocidal molecule, cytotoxic molecule, or anti-inflammatory agent is a cytokine.

6. The conjugate according to claim 4, wherein the conjugate is a fusion protein comprising the antibody molecule and a biocidal molecule, cytotoxic molecule, anti-inflammatory agent, or cytokine.

7. A conjugate comprising an antibody molecule according to claim 1 and a detectable label.

8. A method of treating an inflammatory disorder in a patient comprising administering a therapeutically effective amount of a medicament comprising an antibody molecule or a conjugate comprising said antibody molecule according to claim 1 to the patient.

9. A method of inhibiting angiogenesis in a patient comprising administering a therapeutically effective amount of a medicament comprising an antibody molecule or a conjugate comprising said antibody according to claim 1 to the patient.

10. A method for treating cancer in a patient comprising administering a therapeutically effective amount of a medicament comprising an antibody molecule or a conjugate comprising said antibody according to claim 1 to the patient.

11. A method of delivering a molecule to sites of neovasculature which are the result of angiogenesis, in a patient comprising administering to the patient an antibody molecule according to claim 1, wherein the antibody molecule is conjugated to a molecule selected from the group consisting of biocidal molecule, a cytotoxic molecule, or a radioisotope.

12. A method of imaging, detecting, or diagnosing an inflammatory disorder in a patient comprising administering an antibody molecule or conjugate according to claim 1 to the patient.

13. The method of claim 8, wherein said inflammatory disorder is an autoimmune disorder.

* * * * *